United States Patent
Kitagawa et al.

(10) Patent No.: US 9,096,826 B2
(45) Date of Patent: Aug. 4, 2015

(54) CULTURE SUBSTRATE AND CULTURE METHOD FOR UNDIFFERENTIATED CELL AND UNDIFFERENTIATED CULTURED CELL

(75) Inventors: Fumihiko Kitagawa, Hadano (JP); Takafumi Imaizumi, Hadano (JP); Katsunori Sasaki, Matsumoto (JP)

(73) Assignee: COVALENT MATERIALS CORPORATION, Tokyo (JP)

( * ) Notice: Subject to any disclaimer, the term of this patent is extended or adjusted under 35 U.S.C. 154(b) by 950 days.

(21) Appl. No.: 11/561,055

(22) Filed: Nov. 17, 2006

(65) Prior Publication Data

US 2007/0117204 A1 May 24, 2007

(30) Foreign Application Priority Data

Nov. 22, 2005 (JP) ................................. 2005-336739

(51) Int. Cl.
 *C12N 5/07* (2010.01)
 *C12M 3/00* (2006.01)
 *C12N 5/00* (2006.01)
 *C12N 5/0735* (2010.01)
 *C12N 5/0797* (2010.01)

(52) U.S. Cl.
 CPC ............ *C12N 5/0068* (2013.01); *C12N 5/0606* (2013.01); *C12N 2533/14* (2013.01); *C12N 2533/18* (2013.01)

(58) Field of Classification Search
 CPC .............................. C12N 5/0607; C12M 25/16
 See application file for complete search history.

(56) References Cited

U.S. PATENT DOCUMENTS

| 5,449,620 | A | 9/1995 | Khillan |
| 5,512,474 | A | 4/1996 | Clapper et al. |
| 5,731,417 | A * | 3/1998 | Swiderek et al. ............. 530/356 |
| 6,340,648 | B1 | 1/2002 | Imura et al. |
| 6,667,159 | B1 | 12/2003 | Walt et al. |
| 6,900,055 | B1 | 5/2005 | Fuller et al. |

(Continued)

FOREIGN PATENT DOCUMENTS

| JP | 59-143586 A | 8/1984 |
| JP | 06-007148 A | 1/1994 |

(Continued)

OTHER PUBLICATIONS

SPI Supplies "ANOPORE™ Inorganic Aluminum Oxide Membrane Filters" SPI Supplies Catalog, [online], Structure Probe, Inc., Jan. 17, 2003 [retrieved on May 22, 2009]. Retrieved from the Internet: <URL:http://web.archive.org/web/20030117185743/http://www.2spi.com/catalog/spec_prep/filter2.shtml>, 3 pages.*

(Continued)

*Primary Examiner* — Rosanne Kosson
*Assistant Examiner* — Aaron J Kosar
(74) *Attorney, Agent, or Firm* — Foley & Lardner LLP

(57) ABSTRACT

A culture substrate made of ceramics of any one or more of titania, alumina, zirconia, yttria, and carbon is used where minute pores having a pore diameter of from 0.1 μm to 10 μm are provided at least for a place to which a cell is seeded, and an undifferentiated cell is seeded to at least one place of a surface of the culture substrate, whereby a culture substrate and a culture method for efficiently culturing the undifferentiated cell to be formed into a 3-dimensional cell block shape without causing immune rejection, and an undifferentiated cultured cell.

3 Claims, 3 Drawing Sheets

(56) References Cited

U.S. PATENT DOCUMENTS

| | | | |
|---|---|---|---|
| 7,723,395 | B2 | 5/2010 | Ringeisen et al. |
| 8,262,957 | B2* | 9/2012 | Fukushima et al. ............ 264/42 |
| 2005/0106725 | A1 | 5/2005 | Palecek et al. |
| 2005/0170089 | A1* | 8/2005 | Lashmore et al. ......... 427/248.1 |
| 2005/0230272 | A1 | 10/2005 | Lee et al. |
| 2005/0246021 | A1 | 11/2005 | Ringeisen et al. |
| 2007/0231884 | A1* | 10/2007 | Kitagawa et al. .......... 435/289.1 |
| 2008/0118976 | A1* | 5/2008 | Kitagawa et al. ............. 435/325 |
| 2010/0099547 | A1* | 4/2010 | Fukushima et al. ............ 501/80 |

FOREIGN PATENT DOCUMENTS

| | | | |
|---|---|---|---|
| JP | 2000-157623 | A | 6/2000 |
| JP | 2000-302567 | A | 10/2000 |
| JP | 2001-58885 | A | 3/2001 |
| JP | 2002-17846 | A | 1/2002 |
| JP | 2002-528567 | A | 9/2002 |
| JP | 2002-335949 | A | 11/2002 |
| JP | 3400740 | B2 | 2/2003 |
| JP | 2003-116519 | A | 4/2003 |
| JP | 2005-027598 | A | 2/2005 |
| JP | 2005-253412 | A | 9/2005 |
| JP | 2006-296253 | A | 11/2006 |
| JP | 2006-304734 | A | 11/2006 |
| JP | 2007-167063 | A | 7/2007 |
| JP | 2007-202506 | A | 8/2007 |
| JP | 2007-209203 | A | 8/2007 |
| JP | 2008-148685 | A | 7/2008 |
| JP | 2008-195595 | A | 8/2008 |
| WO | WO 01/36013 | A1 | 5/2001 |
| WO | WO 03/038070 | A1 | 5/2003 |
| WO | WO 2004/048064 | A1 | 6/2004 |

OTHER PUBLICATIONS

Marchi, C.S. and Mortensen, A. "Deformation of Open-Cell Aluminum Foam", Acta Materialia, Nov. 14, 2001, 49(19), 3959-3969.*
Mann, M; Shter, G.E.; Grader, G.S., "Effect of Sintering on TiO2-Impregnated Alumina Foams" J. Mat. Sci, 2002, 37, 4049-4055.*
Li, Shu-Tung; Chen, Hui-Chen; Pierson, Darlene; Yuen, Debbie; and Hansen, Peggy "NuOss®, a Bone Grafting Material for Oral Surgery: Comparative Study with BioOss®", Stoma Science, Jul. 15, 2000, 3 pages.*
Sepulveda, P; Bressiani, A.H; Bressiani, J.C; Meseguer, L; Konig Jr, B, "In Vivo Evaluation of Hydroxyapatite Foams" Mater. Res., 2002, 5(3), 253-256.*
Xinshuang Guo; Zhufa Zhou; Shumei Wang; Song Zhao; Qiang Zhang; Guilin Ma, "A novel method for preparation of interconnected pore-gradient ceramic foams by gelcasting" J. Porous Mater., Oct. 2012 (pub. online Dec. 4, 2011), 19(5), pp. 853-858.*
Nakata, M et al "Fabrication of Porous Alumina Sintered Bodies by Gelate-Freezing Method" J Ceram Soc Japan, 2005, 113(11), pp. 712-715.*
Banhart, John "Manufacture, Characterisation and Application of Cellular Metals and Metal Foams" Progress in Materials Science, 2001, 46, pp. 559-632.*
Coil, "Corrosion Resistance of Continuously Anodised Aluminium" Product Characterization, Part I (1.6), Nov. 2005, pp. 1-10.*
Proceedings of the Japanese Society for Biomaterials Convention, Nov. 28, 2005, vol. 27, p. 301.
M. Dalby et al., "Osteoprogenitor response to defined topographics with nanoscale depths", Biomaterials, Mar. 2006, vol. 27, No. 8, pp. 1306-1315.
F. Kitagawa, U.S. PTO Office Action, U.S. Appl. No. 11/730,705, dated Feb. 23, 2010, 13 pgs.
A. Almirall et al., "Fabrication of low temperature macroporous hydroxyapatite scaffolds by foaming and hydrolysis of an a-TCP paste", Biomaterials, Elsevier Science Publishers B.V., vol. 25, No. 17, Aug. 2004, pp. 3671-3680.
J. Zhang et al., "A comparative study of porous scaffolds with cubic and spherical macropores", Polymer, Elsevier Science Publishers B.V., vol. 46, No. 13, Jun. 17, 2005, pp. 4979-4985.
V. Karageorgiou et al., "Porosity of 3D biomaterial scaffolds and osteogenesis", Biomaterials, Elsevier Science Publishers B.V., vol. 26, No. 27, Sep. 2005, pp. 5474-5491.
Y. Sakka et al., "Fabrication of porous ceramics with controlled pore size by colloidal processing", Science and Technology of Advanced Materials, Elsevier, vol. 6, No. 8, Nov. 2005, pp. 915-920.
F. Kitagawa, U.S. PTO Office Action, U.S. Appl. No. 11/984,544, dated Jun. 8, 2011, 7 pages.
F. Kitagawa, U.S. PTO Office Action, U.S. Appl. No. 11/984,544, dated Dec. 2, 2010, 12 pages.
F. Kitagawa, U.S. PTO Final Office Action, U.S. Appl. No. 11/730,705, dated Sep. 15, 2010, 16 pages.
F. Kitagawa, U.S. PTO Official Action, U.S. Appl. No. 11/984,544, dated Oct. 7, 2014, 17 pages and Oct. 27, 2014, 4 pages.
English Translation of JP 2005-027598 original filed on Nov. 7, 2012, 30 pages.
Y. Josset et al., "In vitro reactions of human osteoblasts in culture with zirconia and alumina ceramics", J. Biomed. Mater. Res., 47, pp. 481-493, 1999.
C. Piconi et al., "Zirconia as a ceramic biomaterial", Biomaterials 20, pp. 1-25, 1999.
I. Inoue et al., "On-Chip culture system for observation of isolated individual cells", Lab on a Chip, pp. 50-55, 2001.

* cited by examiner ured cell in accordance with the present invention is charac-
CULTURE SUBSTRATE AND CULTURE METHOD FOR UNDIFFERENTIATED CELL AND UNDIFFERENTIATED CULTURED CELL

BACKGROUND OF THE INVENTION

1. Field of the Invention

The present invention relates to a culture technology for multipotent undifferentiated cells, such as an ES cell, an adult multipotent stem cell, etc., and particularly relates to a culture substrate and a culture method using this and a cultured cell which forms an undifferentiated 3-dimensional cell block.

2. Description of the Related Art

Damage to a tissue by a disease, aging, an accident, etc. affects human life activity seriously. Regeneration capacity of a human tissue is low. For example, repair of a bone, a cartilage, etc. is carried out by filling a damage portion with an implant, such as an artificial bone.

On the other hand, in a cell culture technique in recent years, due to improvements in development of isolation of an undifferentiated cell from human bone marrow, differentiation and induction into a target tissue cell, a 3-dimensional culture technique, and a scaffold, etc., it is possible to prepare tissues of a skin, a bone, a cartilage, a blood vessel, a cardiac valve, a ligament, etc., from an adult stem cell, and clinical applications have already begun partially.

Thus, in order to obtain a complicated tissue from an undifferentiated cell by way of cell culturing it is necessary to culture the undifferentiated cell represented by an embryonic stem cell whilst maintaining it in an undifferentiated condition, by using a culture substrate having a 3-dimensional structure, to form a 3-dimensional cell block (colony), to supply a cell growth factor and a nutrient to this 3-dimensional cell block, and to differentiate and induce the undifferentiated cell into a target tissue.

In recent years, research of differentiation and induction in the tissue from such an undifferentiated cell has been carried out actively. As an example of this, it is reported that an undifferentiated cell is cultured and proliferated in a porous hydroxyapatite having bio-stability, bio-affinity, and a porosity of 75%, then the porous hydroxyapatite is transplanted in the recipient's bone for therapeutic effects (for example, see Japanese Patent Publication (KOKAI) No. 2002-17846).

Further, in order to culture and maintain the undifferentiated cell represented by the embryonic stem cell etc., a culture substrate is used in which an biopolymer, such as collagen, gelatin, laminin, matrigel, etc., is coated on a plastic petri dish, a feeder cell represented by MEF (murine embryonic fibroblast), is cultured to form a feeder layer onto which an ES cell is seeded (introduced) to be cultured.

It is thought that since calcium phosphate type ceramics, such as a hydroxyapatite, as disclosed in the above-mentioned Japanese Patent Publication No. 2002-17846, is excellent in bio-stability and bio-affinity, it is preferable as a substrate which does not cause immune rejection.

However, $Ca^{2+}$ ion which is the main components of the hydroxyapatite is important factors when an osteoblast forms a bone. Thus, in the case where the calcium phosphate type ceramics, such as the hydroxyapatite etc., are used as the culture substrate for the undifferentiated cells such as the ES cell etc., it is difficult to keep the cells undifferentiated, because they are differentiated and induced into another type of cells due to the influence of Ca2+ ion etc.

Further, in a method of using the feeder cells, such as the above-mentioned MEF etc., the ES cell may not be separated from other cells completely after culturing. Furthermore, it is possible that in the case where the biopolymer or the feeder cell is used as a substrate for regeneration therapy, there is a possibility that it may be contaminated with a dangerous factor or cause immune rejection, and there is a worry that it may provide adverse effects clinically.

For this reason, research and development has been carried out to culture an ES cell on a culture substrate without using the feeder cells, such as MEF, however a undifferentiated complete 3-dimensional culture block has not formed yet.

Therefore, there is a need for developing a culture substrate which can grow a human ES cell etc. efficiently, avoid a dangerous factor and immune rejection, and culture an undifferentiated 3-dimensional cell block.

SUMMARY OF THE INVENTION

In order to solve the above-mentioned technical problems, the present invention aims to provide a culture substrate and a culture method for culturing an undifferentiated cell in which the undifferentiated cell can be cultured efficiently without causing immune rejection, thus being able to form a 3-dimensional cell block, and a 3-dimensional cell block which is cultured while remaining undifferentiated.

The culture substrate for the undifferentiated cell in accordance with the present invention is characterized in that at least one part to which a cell is seeded is ceramics having minute pores with a pore diameter of from 0.1 μm to 10 μm (inclusive).

Such minute pores are formed among particles of the ceramics and exist in the part at which the cell is seeded. Thus, the undifferentiated cell is easily adhered to the culture substrate, circulation of a culture medium is facilitated, and the undifferentiated cell is easily formed into a 3-dimensional cell block shape.

It is preferable that the above-mentioned ceramics should be made of any one or more of titania, alumina, zirconia, yttria, and carbon, which is not likely to cause differentiation and induction of an undifferentiated cell, and excellent in bio-stability and bio-affinity.

Further, it is preferable that the above-mentioned ceramics should be porous ceramics having therein communicating pores.

By providing the communicating pores in the ceramics, the culture can be performed inside the culture substrate, so that more effects can be provided as a scaffold and a culture solution may be circulated suitably.

In addition, by the "pore" is meant here one that is different from the above-mentioned "minute pore".

Further, the above-mentioned porous ceramics is preferably such that countless number of substantially spherical pores are communicated with one another and spread throughout the above-mentioned porous ceramics, the porosity is from 70% to 95% (inclusive), an average pore diameter is from 50 μm to 1000 μm (inclusive), and a diameter of communicating part between adjoining pores is from 10 μm to 200 μm (inclusive).

The porous structure as mentioned above allows the undifferentiated cell to be seeded and fixed to a surface or the pores of the porous ceramics, and proliferated efficiently, and allows a cell growth factor and a nutrient to be supplied efficiently to the undifferentiated cells with which the 3-dimensional cell block is formed.

Further, the culture method for culturing the undifferentiated cell in accordance with the present invention is characterized in that, by using the culture substrates as mentioned above, the undifferentiated cell is seeded to at least one place of a surface or in the pore of the culture substrate, and cultured in an undifferentiated situation to be in the shape of the 3-dimensional cell block.

By using the culture substrate as described above in accordance with the present invention, the 3-dimensional cell block of the undifferentiated cells can be cultured efficiently without causing immune rejection.

In the above-mentioned culture method, it is preferable to seed and culture the undifferentiated cell directly at the ceramics or the ceramic porous body which constitutes the culture substrate.

By directly seeding (introducing) the undifferentiated cell to the ceramics of the culture substrate not via the feeder cell (represented by the MEF), it is possible to obtain the 3-dimensional cell block of the undifferentiated cells, where there is no possibility of being contaminated with a dangerous factor, causing immune rejection, etc.

Further, the undifferentiated cultured cell in accordance with the present invention is characterized by being cultured by means of the above culture substrates, and forming the 3-dimensional cell block.

Such an undifferentiated cultured cell in the shape of the 3-dimensional cell block is supplied with the cell growth factor and the nutrient, and therefore can be differentiated and induced into a target tissue cell, and applied to the regeneration medical treatment of a complicated tissue. Further, the undifferentiated cultured cell in accordance with the present invention is characterized by being cultured by way of the culture methods as described above, to form the 3-dimensional cell block.

Such an undifferentiated cultured cell in the shape of the 3-dimensional cell block as well as the above is useful for the regenerative medical treatment of the complicated tissue.

As described above, using the culture substrate in accordance with the present invention allows the undifferentiated cell to be cultured safely, without differentiating or inducing it and without using the feeder cell, while remaining undifferentiated.

Further, according to the present invention, the cell growth factor and the nutrient can be efficiently supplied to a surface of the ceramics or the cell in the pore, and the 3-dimensional cell block of the undifferentiated cell can be formed.

Therefore, the present invention can contribute to the development of a culture technology for culturing the undifferentiated cell having multipotency, such as the ES cell and an adult multipotent stem cell, as well as to the applications to the regenerative medical treatment of a bionic tissue.

DESCRIPTION OF THE PREFERRED EMBODIMENTS

Figure 1A:
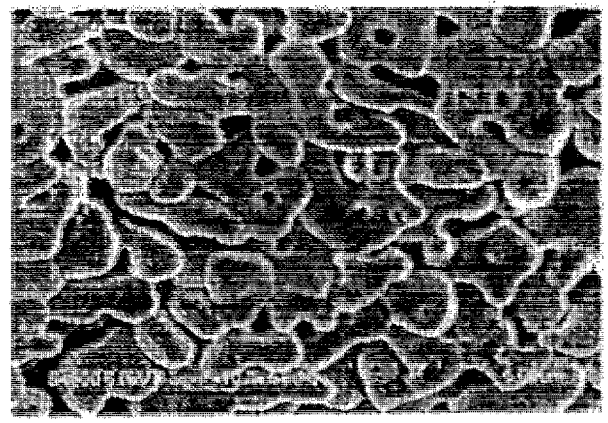
FIG. 1A is an electron micrograph (10000 times magnification) of a titania porous ceramics (sintered body) in accordance with Example 1.

Hereafter, the present invention will be described in detail.

A culture substrate for an undifferentiated cell in accordance with the present invention is characterized in that at least one place to which a cell is seeded is ceramics having minute pores with a pore diameter of from 0.1 µm to 10 µm (inclusive).

Due to such minute pores, the undifferentiated cell is easily adhered to the ceramics, circulation of a culture medium is facilitated, and formation of a 3-dimensional cell block of the undifferentiated cells on a surface of the ceramics (including the inside of a pore when the ceramics is porous) is facilitated.

The above-mentioned minute pores are formed among particles of the ceramics by way of methods of burning off minute chips of organic materials, firing molded ceramics at a low temperature, etc, and may exist partially, however, it is preferable to make them exist throughout the whole ceramics. Through these minute pores, a culture medium can be supplied to the seeded cell 3-dimensionally i.e. from all angles.

From an angle of a meaningful size with respect to adhesion between the cell and a material, the pore diameter of the above-mentioned minute pores is preferably within the above-mentioned limits, and more preferably from 0.1 µm to 5 µm (inclusive).

In addition, the pore diameter of the above-mentioned minute pores can be measured by a method of mercury penetration.

Further, it is preferable that the above-mentioned ceramics should be made of any one or more of titania, alumina, zirconia, yttria, and carbon. These are excellent in bio-stability and bio-affinity, and not likely to cause differentiation and induction of the undifferentiated cell.

Among these, titania, zirconia, and yttria are particularly preferable, with which cultured cells tend to be a spherical block.

It is preferable that the above-mentioned ceramics is a porous ceramics having therein communicating pores.

Since there are the larger pores which are different from the above-mentioned minute pores and which communicate with the outside, the undifferentiated cell enters, and a surface area to fix the cell is enlarged, and also the culture medium is easy to circulate 3-dimensionally.

In the case where the above-mentioned ceramics is porous, it is preferable to have the above-mentioned minute pores at least on an inner surface of the pore. More preferably, the whole porous ceramics has the minute pores.

In addition, a space of the above-mentioned minute pore shall not be included in a pore portion of the porous ceramics here.

The above-mentioned porous ceramics is preferably such that the countless number of substantially spherical pores are communicated with one another and spread throughout the above-mentioned porous ceramics, the porosity is from 70% to 95% (inclusive), the average pore diameter is from 50 µm to 1000 µm (inclusive), and the diameter of communicating part between adjoining pores is from 10 µm to 200 µm (inclusive).

However, the average pore diameter as defined herein does not include the pore diameter of the above-mentioned minute pore, but is the pore diameter taking into consideration only a pore having a larger pore diameter than 10 µm.

Further, the substantially spherical pore is not limited to the complete sphere strictly but meant to include the complete sphere having been somewhat flattened or distorted in shape.

Further, by the communicating part is meant a part where the substantially spherical pores which adjoin each other are in contact with each other to provide an opening. Although the opening may not be circular, it is replaced with a circle which has an area of the opening, and its diameter is expressed as "a diameter of the communicating part" here.

The porous ceramics having the above-mentioned structure allows the undifferentiated cell to be seeded and fixed inside the pores of the porous ceramics, and proliferated on the porous ceramics efficiently, and allows a cell growth factor and a nutrient to be supplied to the undifferentiated cells with which the 3-dimensional cell block is formed.

In addition, the above-mentioned porosity can be derived from a density and a theoretical density of the porous body. Further, the average pore diameter is found by way of a method of resin embedding as disclosed in Japanese Patent No. 3400740, and the diameter of the communicating part may be found by the method of mercury penetration.

When the porosity of the above-mentioned porous ceramics is less than 70%, and when the diameter of an average pore is less than 50 µm, it is difficult to obtain the diameter of the communicating part through which the undifferentiated cell and the culture medium can enter easily.

On the other hand when the above-mentioned porosity exceeds 95% and when the average pore diameter exceeds 1000 µm, the undifferentiated cell entered into the porous ceramics tends to flow out, thus being difficult to fix it on the porous ceramics and also difficult to maintain the shape of the culture substrate.

More preferably, the above-mentioned porosity is from 75% to 90% (inclusive), and still more preferably from 80% to 90% (inclusive). Further, the average pore diameter is more preferably from 250 µm to 800 µm (inclusive).

Further, when the diameter of the communicating part between the pores of the above-mentioned porous ceramics is less than 10 µm, communication performance of the substrate for culturing the cell is insufficient, and the cell growth factor, the nutrient, etc. supplied to the culture medium do not fully spread over the cells, so that there is a possibility that the cell inside the substrate may be extinct or may not be differentiated into the target cell.

On the other hand, in the case where the above-mentioned diameter exceeds 200 µm, the undifferentiated cells entered into the porous ceramics tend to flow out, and it is difficult to fix them on the porous ceramics.

More preferably, the diameter of the above-mentioned communicating part is from 20 µm to 150 µm (inclusive).

In addition, the porous ceramics as described above can be obtained by ceramic foam formed by applying slurry to a sponge-like organic porous body, and burning off the organic porous body, or by way of the method as disclosed in Japanese Patent No. 3400740 in which slurry is stirred to foam then sintered. However, the latter method is more preferable, because it is easy to control the pores.

The cell which is applied to the culture substrate in accordance with the present invention is an undifferentiated cell represented by the ES cell etc. By the undifferentiated cell is meant a cell which is in an undifferentiated condition and has an ability to proliferate into the same cell as itself and an ability to differentiate itself into a tissue cell determined by provision of a cell growth factor. Once it is differentiated into another tissue cell, it cannot return to the undifferentiated condition. In particular, examples of the cell are an embryonic stem cell (ES cell), a mesenchymal stem cell, a hemopoietic stem cell, a neural stem cell, a liver stem cell, a pancreas stem cell, etc. In the present invention, however, it is preferable to use the ES cell and the mesenchymal stem cell, and it is particularly preferably to use the ES cell.

Further, the culture medium used for culturing the cells as described above is not limited particularly, and can be suitably selected according to the cell to be cultured. For example, MEM, α-MEM, DMEM, Eagle's medium, etc. are used suitably.

It is preferable that materials required for maintaining the cells, such as FBS (fetal bovine serum; fetal calf serum), KSR (KnockOut™ Serum Replacement), LIF (leukemia inhibitory factor: leukemia inhibitor), nonessential amino acid, pyruvic acid, an antibiotic, etc. may be added to the culture medium further.

Furthermore, in order to differentiate and induce, into the target cell, the 3-dimensional cell block formed in the undifferentiated condition at the surface of the porous ceramics or in the pores, for example, to induce it into the osteoblast to be a bone, cell growth factors, such as concentration material of FGF (fibroblast growth factor, IGF-1, IGF-II, PDGF (platelet-derived growth factor), TGF-B (transforming growth factor), BMP-Z, HGH, and human growth factor may be added to the culture medium By using the culture substrate in accordance with the present invention, the undifferentiated cell is seeded to at least one place of the surface or in the pore of the above-mentioned ceramics (culture substrate), and the cell growth factor and the nutrient are suitably added to the culture medium to be supplied, so that the undifferentiated culture cell formed in the 3-dimensional cell block can be obtained, while remaining undifferentiated.

Such an undifferentiated culture cell in the shape of the 3-dimensional cell block can effectively be used for the regeneration medical treatment of the complicated tissue.

Especially, when the culture substrate in accordance with the present invention is used, it provides an advantage that a pure undifferentiated cultured cell can be obtained easily, by seeding the undifferentiated cell directly, without forming a feeder layer on the ceramics which are the culture substrate.

Further, the above-mentioned cultured cell can also be obtained as a spherical cell block as shown in the electron micrograph of FIG. 3B (see Example 3 below).

Hereafter, the present invention will be described more particularly with reference to Examples, but the present invention is not limited to the following examples.

EXAMPLE 1

Preparation of Titania Porous Ceramics (Sintered Body)

810 g of titania powder (as a ceramic material) with an average particle diameter of 180 nm, 0.41 g of polycarboxylic acid ammonium salt and 32.4 g of polyethylene imine as dispersing agents, and 270 g of pure water as a dispersion solvent were stirred and mixed with a ball mill for 15 hours, and material slurry was prepared.

To this material slurry, 4.8 g of EMAL™ (registered trademark in Japan, surfactant available from Kao Corporation) as a foaming agent was added and stirred, resulting in foam-like slurry.

Furthermore, 4.2 g sorbitol poly glycidyl ether as a gelling agent was added to the slurry, which was poured into a mould of 150 mm×150 mm×30 mm type, and subjected to humidification/drying to obtain a molded object of a titania porous body.

The molded object was fired at 1200° C. for two hours to obtain a titania porous ceramics (sintered body) of 135 mm×134 mm×21 mm.

A porosity of this sintered body is 84.8%.

Figure 1B:
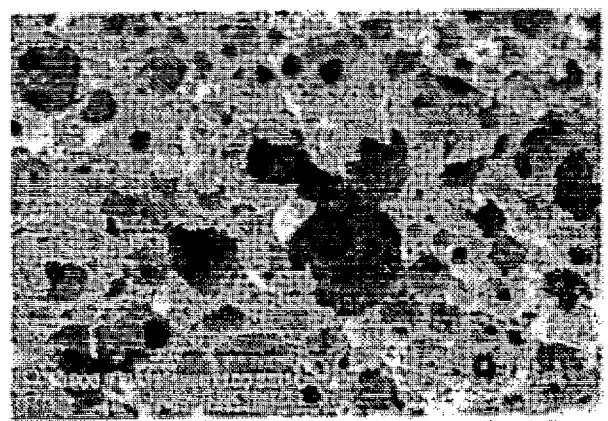
FIG. 1B is an electron micrograph (100 times magnification) of the titania porous ceramics (sintered body) in accordance with Example 1.

Electron micrographs 10000 times magnification, 100 times magnification) of the obtained sintered body are shown FIGS. 1A and 1B.

It was observed, through the electron micrograph shown in FIG. 1A, that there were minute pores having a pore diameter of 0.5-2 μm in a surface of the titania ceramic porous body. The minute pores were measured by the method of mercury penetration, and pore diameters were 0.4-1.0 μm. Further, an average pore diameter was 150-450 μm and a diameter of a communicating part was 40-60 μm.

EXAMPLE 2

A molded object of titania porous body obtained similarly to Example 1 was fired at 1400° C. for two hours, and a titania porous ceramics (sintered body) of 135 mm×134 mm×21 mm was obtained.

A porosity of this sintered body was 80.2%.

Figure 2:
FIG. 2 is an electron micrograph (10000 times magnification) of a titania porous ceramics (sintered body) in accordance with Example 2.

An electron micrograph (10000 times magnification) of the obtained sintered body is shown in FIG. 2. Further, an average pore diameter was 150-450 μm and a diameter of the communicating part was 40-60 μm.

In the electron micrograph as shown in FIG. 2, the minute pores as seen in FIG. 1A has disappeared.

EXAMPLE 3

ES Cell Culturing on Titania Ceramic Porous Body

The titania porous ceramics prepared in Example 1 were worked into a cylindrical shape with a diameter of 5 mm and a height of 2 mm, and inserted into holes of 96-hole plate. Onto the titania porous ceramics, $5.0 \times 10^5$ ES cells cultured beforehand were seeded and cultured for three days at 37° C. in DMEM containing KSR, pyruvic acid, nonessential amino acids, LIF, streptomycin, and penicillin in a 5% $CO_2$ incubator.

Figure 3A:
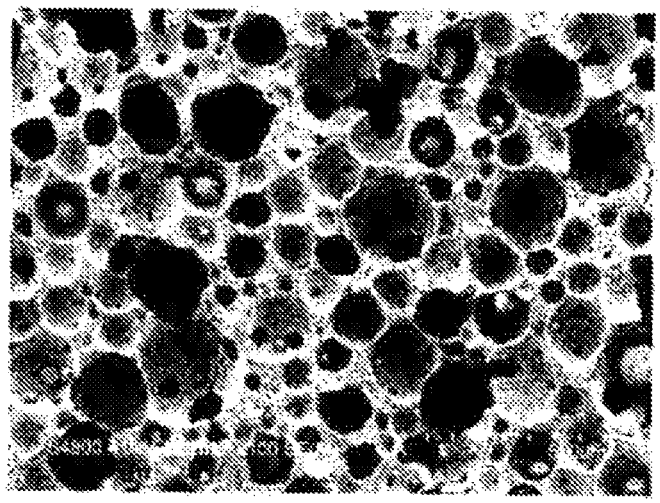
FIG. 3A is an electron micrograph (100 times magnification) of a cell cultured on a titania porous ceramics (sintered body) in accordance with Example 3.
Figure 3B:
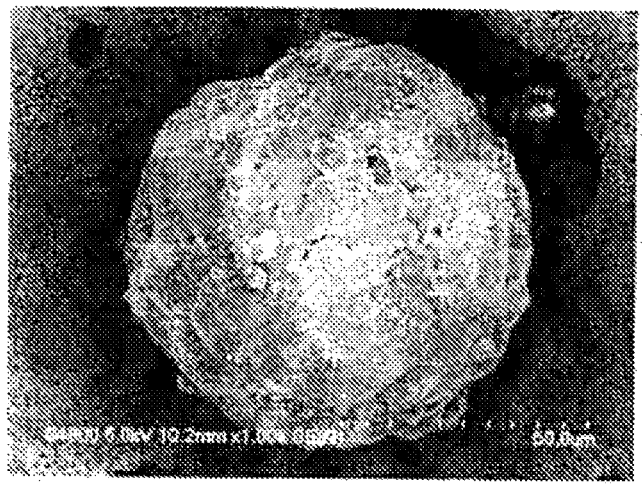
FIG. 3B is an electron micrograph (1000 times magnification) of the cell cultured on the titania porous ceramics (sintered body) in accordance with Example 3.

Electron micrographs (100 times magnification, 1000 times magnification) of the cells after culturing are shown in FIGS. 3A and 3B.

It was confirmed, from the electron micrograph shown in FIG. 3B, that a 3-dimensional cell block was formed on the titania porous ceramics. Furthermore, when the 3-dimensional cell block was dyed with ALP (alkaline phosphatase), it was found that the 3-dimensional cell block was dyed violet and the ES cells proliferated while remaining undifferentiated.

EXAMPLE 4

ES Cell Culturing on Hydroxyapatite Ceramics

A hydroxyapatite ceramic porous body (80% porosity) was used in place of the titania porous ceramics, and the ES cell was cultured similarly to Example 3.

Figure 4:
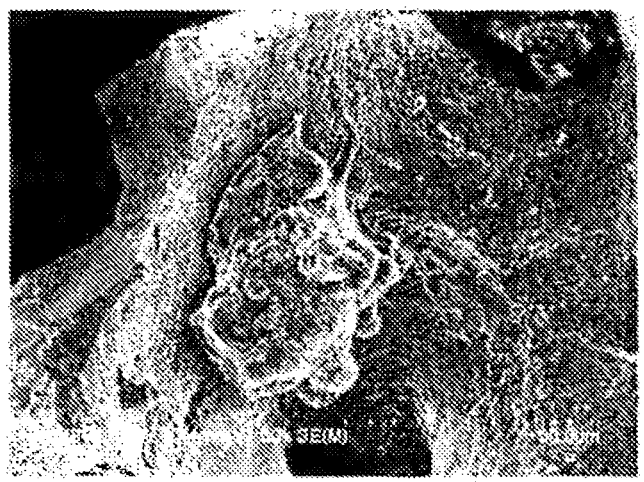
FIG. 4 is an electron micrograph (1000 times magnification) of the cell cultured on hydroxyapatite (sintered body) in accordance with Example 4.

An electron micrograph (1000 times magnification) of the cells after culturing is shown in FIG. 4.

According to the electron micrograph shown in FIG. 4, formation of a 3-dimensional cell block of the ES cells was not found on the hydroxyapatite ceramics.

What is claimed is:

1. A culture substrate for seeding an undifferentiated cell, the culture substrate comprising a porous ceramic body formed from any one or more of titania, alumina, zirconia, yttria, and/or carbon, wherein the porous ceramic body has:
   (a) a porosity from 70% to 95%; and
   (b) a plurality of non-minute and minute pores spread throughout said porous ceramic body in which said plurality of pores are substantially spherical, wherein at least a portion thereof form communications among adjoining non-minute and/or minute pores, and wherein:
      (i) said non-minute pores have an average pore diameter of from 50 μm to 1000 μm;
      (ii) said minute pores have a pore diameter of from 0.1 μm to 10 μm; and
      (iii) said communications among the pores have a diameter from 10 μm to 200 μm.

2. The culture substrate of claim 1, further comprising said undifferentiated cell seeded therein.

3. The culture substrate of claim 1, wherein the pores are arranged to communicate through said communications 3-dimensionally.

* * * * *